United States Patent [19]

Kanno

[11] Patent Number: 4,629,455
[45] Date of Patent: Dec. 16, 1986

[54] MEDICAL INSTRUMENT

[75] Inventor: Michio Kanno, Saitama, Japan

[73] Assignee: Terumo Kabushiki Kaisha, Tokyo, Japan

[21] Appl. No.: 699,588

[22] Filed: Feb. 8, 1985

[30] Foreign Application Priority Data

Feb. 9, 1984 [JP] Japan .................................. 59-16119

[51] Int. Cl.$^4$ ...................... A61M 25/00; F16L 19/02
[52] U.S. Cl. ................................... 604/241; 604/283; 604/905; 285/332
[58] Field of Search ............... 604/283, 905, 241, 242, 604/256; 285/3, 332, 386, 390

[56] References Cited

U.S. PATENT DOCUMENTS

| 3,402,713 | 9/1968 | Senkowski et al. | 604/241 |
| 4,076,285 | 2/1978 | Martinez | 285/332 |
| 4,212,335 | 7/1980 | Bova | 285/332 |
| 4,260,180 | 4/1981 | Halushka et al. | 285/391 |
| 4,346,703 | 8/1982 | Dennehey et al. | 604/244 |
| 4,432,764 | 2/1984 | Lopez | 604/905 |
| 4,433,862 | 2/1984 | Raulins | 285/390 |
| 4,452,473 | 6/1984 | Ruschke | 604/283 |

FOREIGN PATENT DOCUMENTS 2077379 12/1981 United Kingdom .................... 285/3

Primary Examiner—C. Fred Rosenbaum
Assistant Examiner—Michelle N. Lester
Attorney, Agent, or Firm—Frishauf, Holtz, Goodman & Woodward

[57] ABSTRACT

A medical instrument, comprising a female connector member incorporating a female taper portion capable of being joined to a medical instrument member having a male connector member incorporating a male taper portion and a ring member provided to said male connector member so as to encircle said male taper portion and having at least one threaded ridge formed on the inner circumferential surface thereof, which medical instrument is characterized by having formed on the outer periphery of said female connector member at least one threaded groove capable of being helically fitted on said threaded ridge of said ring member and having formed at a desired position in said threaded groove a rib adapted to engage with said threaded ridge when said threaded groove is being helically fitted on said threaded ridge. The first medical instrument member is, for example, a three-way faucet, and the second medical instrument member is, for example, an artificial organ such as a Ruer port connector and an artificial lung, catheters, blood circuits for the artificial organs.

21 Claims, 7 Drawing Figures

MEDICAL INSTRUMENT

BACKGROUND OF THE INVENTION

1. Field of the Invention

This invention relates to a medical instrument. More particularly, this invention relates to a medical instrument possessed of a highly reliable connecting part which can be firmly joined.

2. Description of the Prior Art

Various medical instruments such as injection syringes (consisting of a barrel fitted with a plunger and a hollow needle), catheters of varying types, and artificial organs which are in popular use are possessed of a female connector member incorporating a female taper portion and a male connector member incorporating a male taper portion capable of being fitted into the female taper portion.

FIG. 1 illustrates a typical connecting portion which comprises a female connector member 1 incorporating a female taper portion 1a and having a screw thread 1b formed monolithically on the outer periphery thereof and a male connector member 2 incorporating a male taper portion 2a and having a ring member 2c monolithically formed on the outer side thereof and a screw thread 2b formed monolithically on the inner side thereof, so that the female connector member 1 and the male connector member 2 can be firmly and safely joined by fitting the male taper portion 2a into the female taper portion 1a and helically fitting the screw thread 1b into the screw thread 2b. Since the female connector member 1 and the male connector member 2 illustrated in FIG. 1 have their screw threads 1b and 2b formed monolithically thereon, however, the angle and position of connection in the relative rotational directions around their axes cannot be selected at will at the time the connector members are joined to each other, and they are sometimes loosened.

FIG. 2 illustrates a medical instrument which comprises a medical instrument member Y and a medical instrument member X, the member Y having a female connector member 3 incorporating a female taper portion 3a and having a stationary screw thread 3b formed on the outer periphery thereof and the member X having a male connector member 4 incorporating a male taper portion 4a and having rotatably mounted on the outer periphery thereof a rotary ring 5 incorporating a rotary screw thread 5a so that the rotary ring 5 is prevented from moving in the axial direction toward the leading end of the medical instrument by the union between the rotary ring 5 and an engaging portion 4c of the male connector member 4. In this arrangement, the female connector member 3 and the male connector member 4 are enabled to join each other by fitting the male taper portion 4a into the female taper portion 3a and, at the same time, helically fitting the rotary screw thread 5a into the stationary screw thread 3b. In the case of the female connector member 3 and the male connector member 4 illustrated in FIG. 2, the angle and position of connection in their relative rotational directions around their axes can be selected at will because the rotary ring 5 is rotatably mounted relative to the male connector member 4. Owing to this merit, the union of the connector members 3 and 4 can be advantageously utilized in a medical instrument such as a three-way faucet for which directionality counts much.

In the example illustrated in FIG. 2, the union of the member X and the member Y of the medical instrument is accomplished by bringing the male taper portion 4a and the female taper portion 3a into mutual contact. The helical engagement between the rotary screw thread 5a of the rotary ring 5 and the stationary screw thread 3b, therefore, is adapted to avoid interfering with the coming into contact of the aforementioned taper portions 4a and 3a. As the result, the surface area of contact between the stationary screw thread 3b of the female connector member 3 and a rotary screw thread 5a of the rotary ring 5 and the surface area of contact between the engaging portion 4c of the male connector member 4 and the rotary ring 5 are both small and the rotary ring 5 is liable to produce idle rotation relative to the female connector member 3 and the male connector member 4. When the engagement between the female taper portion 3a and the male taper portion 4a becomes loose, the pressure of the fluid flowing inside the member Y of the medical instrument exerts a force tending to urge the member X of the medical instrument outwardly. It is for the purpose of preventing the otherwise possible separation of the member X in this case that the present medical instrument is furnished with the rotary ring 5 at all. Since the rotary ring 5 has a small surface area of contact and is liable to generate idle rotation as described above, it is eventually rotated in the direction of separation by the aforementioned outwardly urging force. It is, therefore, difficult for the helical engagement between the stationary screw thread 3b of the female connector member 3 and the rotary screw thread 5a of the rotary ring 5 to ensure preclusion of the possibility of separation between the female taper portion 3a of the female connector member 3 and the male taper portion 4a of the male connector member 4.

In illustrated the example illustrated FIG. 2, there may be conceived an idea of adapting a shaft 6 of the male connector member 4 and a hole 7 of the rotary ring 5 so that they have mutually ground surfaces for safer union. In this case, however, the male connector member 4 detracts from smoothness of rotation relative to the rotary ring 5 and the male connector member 4 experiences difficulty in securing free directionality. Thus, this idea proves unsatisfactory. Alternately, there may be conceived an idea of adapting the stationary screw thread 3b of the female connector member 3 and the rotary screw thread 5a of the rotary ring 5 so as to have mutually ground thread surfaces for safer union. In this case, the stationary screw thread 3b of the female connector member 3 and the rotary screw thread 5a of the rotary ring which have their thread surfaces ground against each other are required to be used as pair at all times. Incidentally, the female connector member 3 and the male connector member 4 are intended to be joined in a freely selected combination. Thus, there are times when the female connector member 3 and the male connector member 4 randomly selected cannot be solidly and safely joined to each other because their screw threads fail to form the pair mentioned above.

An object of this invention, therefore, is to provide a novel medical instrument.

Another object of this invention is to provide a medical instrument to connect both of the medical instrument members X shown in the prior art which enables the female connector member and the male connector member to be firmly and safely joined, and a medical instrument fitting the medical instrument members.

SUMMARY OF THE INVENTION

The objects described above are attained by a medical instrument, comprising a female connector member incorporating a female taper portion capable of being joined to a medical instrument member having a male connector member incorporating a male taper portion and a ring member provided to to the male connector member so as to encircle the male taper portion and having at least one threaded ridge formed on the inner circumferential surface thereof, which medical instrument is characterized by having formed on the outer periphery of the female connector member at least one threaded groove capable of being helically fitted on the threaded ridge of the ring member and having formed at a desired position in the threaded groove a rib adapted to engage with the threaded ridge when the threaded groove is being helically fitted on the threaded ridge.

The objects described above are also attained by a medical instrument, comprising a first medical instrument member having a male connector member incorporating a male taper portion and a ring member provided to to the male connector member so as to encircle the male taper portion and having at least one threaded ridge formed on the inner circumferential surface thereof and a second medical instrument member having a female connector member incorporating a female taper portion capable of being joined to the first medical instrument member, which medical instrument is characterized by having formed on the outer periphery of the female connector member at least one threaded groove capable of being helically fitted on the threaded ridge of the ring member and having formed at a desired position in the threaded groove or a threaded groove of the first medical instrument member a rib adapted to engage with the threaded ridge when the threaded groove is being helically fitted on the threaded ridge.

This invention also relates to a medical instrument wherein the rib in the threaded groove is placed into engagement with the threaded ridge by being deformed upon helical engagement with the threaded ridge. This invention relates further to a medical instrument wherein the female taper portion and the male taper portion mentioned above are each provided with a Luer-type taper surface. This invention relates further to a medical instrument wherein the threaded groove has portion thereof missing in the circumferential direction. This invention further relates to a medical instrument wherein the rib is formed of a material softer than the material of the threaded ridge of the rotary ring. Further this invention relates to a medical instrument wherein the rib has a thickness in the range of 0.15 to 1.50 mm. This invention also relates to a medical instrument wherein a plurality of ribs are disposed as suitably separatus in the threaded groove. This invention relates to a medical instrument wherein the rib is provided at a position spaced from a little from a starting end in the threaded groove.

EXPLANATION OF PREFERRED EMBODIMENTS

Figure 1:
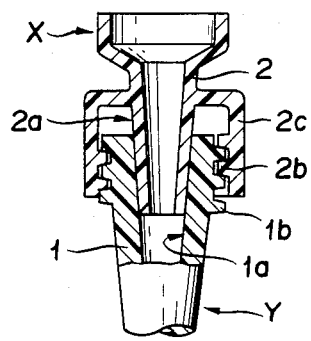
FIG. 1 is a cross-sectional view illustrating a typical conventional medical instrument.
Figure 2:
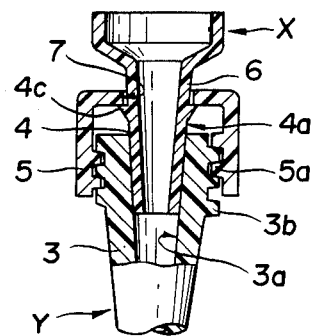
FIG. 2 is a cross-sectional view illustrating another typical conventional medical instrument.
Figure 3:
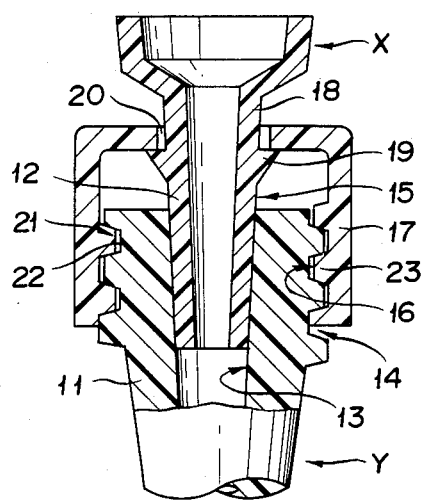
FIG. 3 is a cross-sectional view illustrating an embodiment of a medical instrument according to the present invention.

Now, one embodiment of this invention will be described below with reference to the accompanying drawings. The medical instrument according to the present invention comprises a first medical instrument member X and a second medical instrument member Y. As the typical medical instrument member X, there is a member which has a connecting portion as shown in FIGS. 1 and 2, and a connecting tube having a three-way faucet and the like. And as the typical medical instrument member Y, there is a medical instrument having a port portion for connecting the medical instrument member X, and concretely there are artifical organs such as a Luer connector haivng a blood collecting port portion, a catheter having a injection port for a medical solution, an artifical lung having a blood collecting port; a blood circuit having a blood collecting port or a medical solution injecting port and the like. A female connector member 11 of the second member Y constitutes a female taper portion 13 forming a Luer taper surface and a screw thread 14 formed monolithically on the outer periphery of the female taper portion 13. The first member X possesses a male connector member 12. This male connector member 12 is provided with a male taper portion forming a Luer tape surface capable of engaging with the female taper portion 13. It further has rotatably mounted on the outer periphery of a neck portion 18 thereof a rotary ring 17 which is provided with a rotary screw thread 16 capable of being helically engaged with the stationary screw thread 14. And the rotary 17 may be a ring member monolithically formed with the male taper portion as shown in FIG. 1. Hereinafter, the ring member is explained by the example of the rotary ring. The aforementioned rotary ring 17 is enabled to prevent the male connector member 12 from moving in the axial direction toward the leading end thereof owing to the engagement of the rotary ring 17 with an engaging portion 19 formed on the outer periphery of the neck portion 18 on the leading end side thereof in the axial direction of the male connector member 12. The rotary ring 17 is adapted to be attached fast to the neck portion 18 of the male connector member 12 by causing a hole 20 formed at the center of the rotary ring to be passed on the male connector member 12 inwardly from the leading end side thereof in the axial direction and slid over the engaging portion 19 by virtue of mutual elastic deformation of the engaging portion 19 and the hole 20.

In the present embodiment, the stationary screw thread 14 of the female connector member 11 is provided with a threaded groove 21 and this threaded groove 21 is provided at a desired position in the lead direction thereof with a rib 22 crossing the threaded groove 21. Number of threaded groove 21 may be number enough to connect the threaded ridge 23 of the medical instrument member X, preferably the same. It may be plural, preferably two. This rib 22 is adapted to be fractured by the threaded ridge 23 of the rotary screw thread 16 at the time the stationary screw thread 14 of the female connector member and the rotary screw thread 16 of the rotary ring 17 are in the process of being helically engaged. The fractured rib 22 is brought into pressed engagement with the threaded ridge 23. The rib 22 in the present embodiment is formed throughout the entire depth of the threaded groove 21 of the stationary screw thread 14.

The rib 22 is formed either of the same material as the threaded ridge 23 of the rotary screw thread 16 or of a material softer than the material of the threaded ridge 23. Examples of the material of the rib include polycarbonate, polyethylene, polyester, polyamide, polyacetal and ABS resin. Owing to this selection of the material for the rib, the rib 22 is fractured rather easily by the threaded ridge 23 and the fractured rib is easily brought into tight engagement with the threaded ridge 23. Because of the tightness of this engagement, ample frictional force is produced between the fractured rib 22 and the threaded ridge 23.

Figure 4:
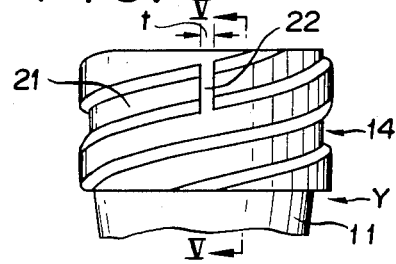
FIG. 4 is a front view illustrating the essential part of a female connector member of the medical instrument illustrated in FIG. 3.
Figure 5:
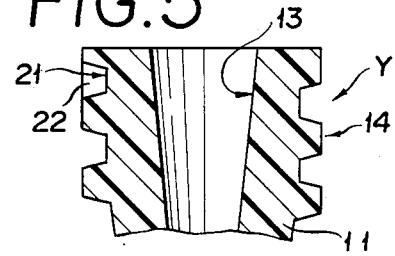
FIG. 5 is a cross-sectional view taken through FIG. 4 along the line V—V.

The thickness of the rib 22 in the lead direction as illustrated in FIG. 4 is desired to fall in the range of 0.15 to 1.50 mm. Because of the limited thickness, the rib 22 is fractured relatively easily by the threaded ridge 23 and the necessary frictional force is obtained between the fractured rib 22 and the threaded ridge 23. And the position of the rib 22 is preferably spaced a little from a starting end in the threaded groove 21 to a direction of a finishing end as shown in FIG. 4. When the rib 22 is provided at the position spaced a little from the starting end to the direction of the finishing end, the threaded ridge 23 of the rotary ring can be easily inserted at its position, so initial insertion of the rotary ring into the threaded groove becomes easy.

In the second medical instrument member Y to which the embodiment described above is applied, the female connector member 11 is enabled to be joined with the male connector member 12 of the first medical instrument member X by fitting the female taper portion 13 on the male taper portion 15 of the first medical instrument member X and, at the same time, helically fitting the threaded groove 21 of the stationary screw thread 14 on the threaded ridge 23 of the rotary screw thread 18 of the rotary ring 17 of the first medical instrument member X. During the helical engagement between the stationary screw thread 14 and the rotary screw thread 16 of the rotary ring 17, the rib 22 formed in the threaded groove 21 of the stationary screw thread 14 is fractured by the threaded ridge 23 of the rotary screw 23 and, consequently, the fractured rib 22 and the threaded ridge 23 of the rotary screw thread 16 give rise to powerful pressed contact. In the presence of the pressed contact between the aforementioned rib 22 and the threaded ridge 23 of the rotary screw thread 16, the stationary screw thread 14 of the female connector member 11 is enabled to bring the opposite thread surface of the aforementioned rib 22 into powerful face contact with the opposed thread surface of the rotary screw thread 16.

In the second medical instrument member Y, therefore, generation of strong frictional resistance is attained between the stationary screw thread 14 of the male connector member 12 and the rotary screw thread 16 of the rotary ring 17 without readily allowing the rotary ring 17 to produce idle rotation relative to the female connector member 11 and the male connector member 12 owing to the powerful pressed contact between the aforementioned rib 22 and the threaded ridge 23 of the rotary screw thread 16 and the powerful face contact between the opposite side thread surface of the rib 22 in the stationary screw thread 14 and the opposed thread surface of the rotary screw thread 16. As the result, the otherwise possible separation of the union between the female taper portion 13 of the female connector member 11 in the second medical instrument member Y and the male taper portion 15 of the male connector member 12 in the first medical instrument member X is safely prevented because of the maintenance of the stable engagement between the statioary screw thread 14 of the female connector member 11 in the second medical instrument member Y and the rotary screw thread 16 of the rotary ring 17 in the first medical instrument member X.

Furthermore, since the rotary ring 17 of the first medical instrument member X to which the second medical instrument member Y is to be joined is mounted rotatably relative to the male connector member 12, the angular positions of connection in the relative rotational directions about the axis of the female connector member 11 of the second medical instrument member Y and the male connector member 12 of the first medical instrument member can be freely adjusted.

In an experiment in which the rib 22 of the aforementioned embodiment was formed of polycarbonate and the thickness of this rib in the lead direction thereof was fixed at 0.30 mm, it was confirmed that the rib 22 was easily fractured by normal tying force exerted on the rotary ring 17 and powerful, reliable connection was obtained between the female connector member 11 and the male connector member 12.

Alternatively, a stationary screw thread may be formed on either of the female connector member and the male connector member and a rotary ring incorporating a rotary screw thread may be formed on the other of the aforementioned two connectors.

Optionally, a rib may be disposed in the threaded groove of at least either of the stationary screw thread and the rotary screw thread.

For the present invention, ribs may be disposed one each at a plurality of positions in the lead direction of the threaded ridge.

Figure 6:
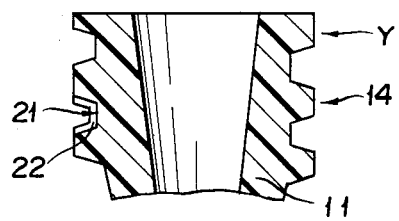
FIG. 6 is a cross-sectional view illustrating another embodiment of the present invention.

Furthermore, a rib 22 of the shape illustrated in FIG. 6 may be disposed only in the range conforming to the contour of the threaded groove 21 of the stationary screw thread 14. Otherwise, there may be disposed a rib which conforms only to the bottom side of the threaded groove 21.

For this invention, the stationary screw thread and/or the rotary screw thread may have part thereof missing in the circumferential direction.

Figure 7:
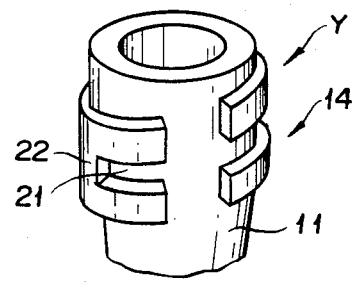
FIG. 7 is a perspective view illustrating yet another embodiment of this invention.

FIG. 7 illustrates a modification, wherein the screw thread of the female connector member 11 has a missing part in the portion thereof which corresponds to the parting line of a sectional die during the molding of the female connector member.

As described above, the medical instrument of the present invention comprises a female connector member incorporating a female taper portion capable of being joined to a first medical instrument member having a male connector member incorporating a male taper portion and a ring member provided to the male connector member so as to encircle the male taper portion and having at least one threaded ridge formed on the inner circumferential surface thereof, which medical instrument is improved by having formed on the outer periphery of the female connector member at least one threaded groove capable of being helically fitted on the threaded ridge of the ring member and having formed at a desired position in the threaded groove a rib adapted to engage with the threaded ridge when the threaded groove is being helically fitted on the threaded ridge. Thus, the angular position of connection between the female connector member and the male connector member can be freely selected and the female conenctor member and the male connector member can be joined firmly with high reliability.

Furthermore, the rib in the threaded groove is adapted to be deformed upon helical engagement thereof with the threaded ridge and consequently brought into tight engagement with the threaded ridge, the female taper portion and the male taper portion are provided with matched Luer surfaces, the aforementioned threaded groove is adapted to have part thereof missing in the circumferential direction, and the aforementioned rib is formed of a material softer than the material of the opposed threaded ridge. As the result, the rib is relatively easily fractured by the opposed threaded ridge and the fractured rib and the opposed threaed ridge easily form safe, intimate union enough to generate ample frictional force between the fractured rib and the opposed threaded ridge.

Furthermore, since the thickness of the aforementioned rib is 0.15 to 1.50 mm, the rib is relatively easily fractured by the opposed threaded ridge and the fractured rib and the opposed threaded ridge are consequently allowed to generate necessary frictional force therebetween.

Optionally, a plurality of ribs may be disposed as suitably separated in the threaded groove. Further, the rib may be provided at a threaded grooved formed between the threaded ridges of an inner surface of the rotary ring of the first medical instrument member.

What is claimed is:

1. A connector comprising
   a female member including a female taper portion;
   a male member including a male taper portion tightly accommodated in said female member;
   a ring member encircling the tapered portion of said male member;
   one of said ring member and said female member having a ridge for cooperating with a threaded, helical groove on the other of said ring member and said female member to tighten the male member into the female member as the ring is turned and thereby screwed onto the female member; and
   an element integral with said other of said ring member and said female member, traversing at least part of the width of said groove and extending into said groove from at least one wall of said groove so as to frictionally grip said ridge as the ring is turned to screw the ring onto the female member, said element having a thickness such that the element can yield laterally to an engaging force of the ridge.

2. The connector of claim 1, wherein said element is deformed by said ridge as said ring member is turned.

3. The connector of claim 2, wherein said element is more flexible than said ridge.

4. The connector of claim 3, wherein said element has a thickness in the range of 0.15 to 1.50 mm.

5. The connector of claim 2, wherein at least part of said element is fractured by said ridge.

6. The connector of claim 2, wherein said element is a rib extending transversely between the walls of said groove.

7. The connector of claim 6, wherein the ridge is threaded on the inner circumferential surface of said ring member and the groove is formed on the outer periphery of said female member.

8. The connector of claim 6, wherein said ring member is rotatable relative to said male member and engages a shoulder on said male member as the ring member is screwed onto the female member.

9. The connector of claim 1, wherein said ring member is rotatable relative to said male member and engages a shoulder on said male member as the ring member is screwed onto the female member.

10. The connector of claim 1, wherein said male and female taper portions include Luer-type surfaces.

11. The connector of claim 1, wherein said element is spaced from the point where the ridge and groove come into initial contact as the ring member is screwed onto the female member.

12. The connector of claim 11, wherein a plurality of elements are provided in the groove and are spaced from each other.

13. The connector of claim 7, wherein said element is spaced from the point where the ridge and groove come into initial contact as the ring member is screwed onto the female member.

14. The connector of claim 1, wherein a plurality of elements are provided in the groove and are spaced from each other.

15. The connector of claim 1, wherein said element projects from the bottom of said groove.

16. A connector comprising
    a female member including a female taper portion;
    a male member including a male taper portion tightly accommodated in said female member;
    a ring member encircling the tapered portion of said male member;
    one of said ring member and said female member having a ridge for cooperating with a threaded, helical groove on the other of said ring member and said female member to tighten the male member into the female member as the ring is turned and thereby screwed onto the female member; and
    an element integral with said other of said ring member and said female member, traversing at least part of the width of said groove and extending into said groove from at least one wall of said groove so as to frictionally grip said ridge as the ring is turned to screw the ring onto the female member, said element having a thickness less than the circumference of said other of said ring member and said female member.

17. The connector of claim 16, wherein said thickness is less than the width of said groove.

18. The connector of claim 17, wherein said element is a rib extending transversely between the walls of said groove.

19. The connector of claim 16, wherein said element s spaced from the point where the ridge and groove come into initial contact as the ring member is screwed onto the female member.

20. The connector of claim 16, wherein a plurality of elements are provided in the groove and are spaced from each other.

21. The connector of claim 16, wherein said element projects from the bottom of said groove.

* * * * *